US006165723A

United States Patent [19]
Shah et al.

[11] Patent Number: 6,165,723
[45] Date of Patent: Dec. 26, 2000

[54] IN SITU HYBRIDIZATION METHOD FOR DETECTING TARGET NUCLEIC ACID

[75] Inventors: Jyotsna S. Shah, Nashua, N.H.; Nick S. Harris, Las Gatos, Calif.

[73] Assignee: Igenex, Inc., Palo Alto, Calif.

[21] Appl. No.: 09/313,852

[22] Filed: May 18, 1999

Related U.S. Application Data

[60] Provisional application No. 60/088,561, May 18, 1998.

[51] Int. Cl.[7] .............................. C12Q 1/68; G01N 1/30; C07H 21/04
[52] U.S. Cl. ..................... 435/6; 435/40.5; 435/40.51; 536/24.32
[58] Field of Search .................... 435/6, 40.5, 40.51; 536/24.32

[56] References Cited

U.S. PATENT DOCUMENTS

| | | | |
|---|---|---|---|
| 4,886,741 | 12/1989 | Schwartz | 435/5 |
| 5,447,841 | 9/1995 | Gray et al. | 435/6 |
| 5,506,098 | 4/1996 | Zarling et al. | 435/6 |
| 5,521,061 | 5/1996 | Bresser et al. | 435/5 |
| 5,582,982 | 12/1996 | Cubbage et al. | 435/6 |
| 5,582,985 | 12/1996 | Thompson | 435/6 |
| 5,750,340 | 5/1998 | Kim et al. | 435/6 |
| 5,888,733 | 3/1999 | Hyldig-Nielsen et al. | 435/6 |

FOREIGN PATENT DOCUMENTS

WO 90/02173   3/1990   WIPO.

OTHER PUBLICATIONS

Holland, M.S. et al. J. Histochem. Cytochem. 44(3):259–265, Mar. 3, 1996.
DeLong and Shah, *Diag. Clin. Testing 28*: 41–44 (1990).
DeLong et al., *Science 243*: 1360–1363 (1989).
Frischner et al., *Can. J. Microb. 42*: 1061–1071 (1996).
Krause et al., *J. Clin. Microbiol. 34*: 2014–2016 (1996).
Leidtke et al., *PCR Methods and Applications 3*: 301–304 (1994).
Shah et al., *Clin. Diag. Lab. Immunol. 3*: 119–127 (1996).
Amann et al., *J. Bacteriol. 172*: 762–770 (1990).
Erlandsen et al., (1993) Molecular approach to the speciation and detection of Giardia: fluorochrome–rDNA probes for identification of Giardia lamblia, Giardia Muris, and Giardia ardeae in laboratory and environmental samples by in–situ hybridization. In *Giardia —from Molecules to Disease and Beyond*, CAB International. pp 64–66.
Roller et al., *Microbiology 140*: 2849–2858 (1994).

*Primary Examiner*—Carla J. Myers
*Assistant Examiner*—Diana Johannsen
*Attorney, Agent, or Firm*—Kevin M. Farrell

[57] ABSTRACT

The present invention provides a method for detecting a target nucleic acid fragment directly from a specimen obtained from a patient by in situ hybridization. The method is comprised of several steps which are performed in the listed order. A sample of the specimen is deposited onto a slide. The sample is fixed onto the slide with fixative, the fixative comprising either methanol-acetic acid at a ratio of from 99:1 to 80:20, or formalin-acetic acid at a ratio of from 99:1 to 80:20. The nucleic acids of the fixed sample are contacted with a probe complex specific for the target nucleic acid fragment, under conditions appropriate for hybridization. Non-hybridized probe complex is rinsed from the sample. The rinsed sample is stained with Evans Blue. The hybridized probe complex is visually detected by microscopy, with the presence of the probe complex being an indication of the presence of the target nucleic acid fragment. The method can be performed with different hybridization buffers, several of which are disclosed. The method of the present invention is useful for detecting pathogens in a specimen. Specific probe complexes are disclosed which are useful for detecting pathogens of the species Babesia. The method is useful in detecting nucleic acids from a wide variety of specimens, including serum, plasma, sputum, urine, cerebral spinal fluids, tissue, breast milk, and insects such as ticks.

26 Claims, No Drawings

SEQUENCE LISTING

```
<160> NUMBER OF SEQ ID NOS:  8

<210> SEQ ID NO 1
<211> LENGTH: 22
<212> TYPE: DNA
<213> ORGANISM: Babesia microti

<400> SEQUENCE: 1
gccacgcgaa aacgcgcctc ga                                              22

<210> SEQ ID NO 2
<211> LENGTH: 18
<212> TYPE: DNA
<213> ORGANISM: Babesia microti

<400> SEQUENCE: 2
gccacgcgaa aacgcgcc                                                   18

<210> SEQ ID NO 3
<211> LENGTH: 20
<212> TYPE: DNA
<213> ORGANISM: Babesia microti

<400> SEQUENCE: 3
```

-continued

```
aataaacgcc acgcgaaaac                                              20

<210> SEQ ID NO 4
<211> LENGTH: 23
<212> TYPE: DNA
<213> ORGANISM: Babesia microti

<400> SEQUENCE: 4
gccacgcgaa aacgcgcctc gag                                          23

<210> SEQ ID NO 5
<211> LENGTH: 18
<212> TYPE: DNA
<213> ORGANISM: Babesia WA-1

<400> SEQUENCE: 5
aataaacgca gccaagac                                                18

<210> SEQ ID NO 6
<211> LENGTH: 20
<212> TYPE: DNA
<213> ORGANISM: Babesia WA-1

<400> SEQUENCE: 6
aataaacgca gccaagacag                                              20

<210> SEQ ID NO 7
<211> LENGTH: 33
<212> TYPE: DNA
<213> ORGANISM: Babesia microti

<400> SEQUENCE: 7
ataggtcaga aacttgaatg atacatcgcc ggc                               33

<210> SEQ ID NO 8
<211> LENGTH: 24
<212> TYPE: DNA
<213> ORGANISM: Babesia microti

<400> SEQUENCE: 8
gttatagttt atttgatgtt cgtt                                         24
```

IN SITU HYBRIDIZATION METHOD FOR DETECTING TARGET NUCLEIC ACID

This Application claims priority to U.S. Provisional Application No. 60/088,561, filed May 18, 1998.

BACKGROUND OF THE INVENTION

Hybridization traditionally is understood as the process which, under predetermined reaction conditions, two partially or completely complimentary strands of deoxyribonucleic acid molecules (DNA), ribonucleic acid molecules (RNA), and combinations of DNA and RNA, are separated into single strands and then allowed to anneal forming base-paired double helices. The term in situ hybridization, as used herein, refers to a hybridization technique which effectively detects specific nucleic acid sequences in intact cells or tissues. The technique of in situ hybridization provides the added benefit of also yielding morphological information about the individual intact cells.

In situ hybridization technique was first described by Gall and Padre (*Proc. Nat. Acad Sciences* 63: 378–83 (1969)) and Jone et al. (*Nature* 225: 946–8 (1969)). Both groups looked at formation and detection of RNA-DNA hybrids in cytological preparations using radiolabeled probes. The technique permits detection of DNA or RNA in individual cells which contain specific sequences, in a heterogeneous cell population. It also allows the simultaneous determination of biochemical and morphological characteristics of the examined cells. Since its initial description, in situ hybridization has undergone continuous evolution in methodology and application. At present the technique has direct applications in many areas of biomedical and clinical research including cell biology, clinical diagnosis, developmental biology, genetics and virology.

SUMMARY OF THE INVENTION

One aspect of the present invention is a method for detecting a target nucleic acid fragment directly from a specimen obtained from a patient by in situ hybridization. The method is comprised of several steps which are performed in the listed order. A sample of the specimen is deposited onto a slide. The sample is fixed onto the slide with fixative, the fixative comprising either methanol-acetic acid at a ratio of from 99:1 to 80:20, or formalin-acetic acid at a ratio of from 99:1 to 80:20. The nucleic acids of the fixed sample are contacted with a probe complex specific for the target nucleic acid fragment, under conditions appropriate for hybridization. Non-hybridized probe complex is rinsed from the sample. The rinsed sample is stained with Evans Blue. The hybridized probe complex is visually detected by microscopy, with the presence of the probe complex being an indication of the presence of the target nucleic acid fragment. Different embodiments include use of the method with different hybridization buffers. In one embodiment, the hybridization buffer consisting essentially of from 10% to 50% formamide, 2×SSC (pH 7.4), 1% NP40, is used. In another embodiment, the hybridization buffer consisting essentially of 1.5 M to 4 M GuSCN buffer is used. In another embodiment, the hybridization buffer consisting essentially of 2 M to 6 M GuHCL buffer is used. Other embodiments of the invention involve the use of specific probes for the identification of pathogens of the species Babesia, in a sample. Other embodiments include detecting nucleic acids from a wide variety of specimens, including serum, plasma, sputum, urine, cerebral spinal fluids, tissue, breast milk, and insects such as ticks.

DETAILED DESCRIPTION OF THE INVENTION

The present invention is based on the discovery of an improved method for directly detecting the presence of a target nucleic acid in cells of specimens obtained from a patient (e.g. blood smears, paraffin embedded tissues, and ticks), by in situ hybridization. The invented method is particularly well suited for detecting nucleotide sequences specific to pathogens, which are found within whole blood cells or infected tissues, using oligonucleotide probes, special pre-hybridization fixation solutions, post hybridization fixation solutions and protocols. More specifically novel improvements of the traditional fixation/pretreatment methods are described which employ organic and in-organic compounds which selectively allow the oligonucleotide probes to penetrate inside the pathogens, both bacterial and protozoan, which are located inside the infected cells. In addition, a post fixation procedure with Evans Blue after hybridization with fluorescence labeled probe, allows the organisms which retain the hybridized probes to be easily visualized within the blood cells.

The novel and unique in situ hybridization and detection technique described herein is a protocol which allows the use of recombinant DNA or RNA probes with cells, microorganisms, or tissue sections, and is compatible with microscopic examination routinely performed in bacteriology, parasitology, histology or pathology laboratories. The present invention applies a nucleic acid probe of predetermined nucleotide sequence to the sample cells (or tissue) and to the examination of the sample by microscopy to determine which cells (or tissues) within the population contain the specific nucleic acid sequences of interest. Thus, in infected whole blood smears or tissue sections, pathogenic organisms such as bacteria, virus, protozoan, or fungi, can be detected within the infected cells. Such protocols provide useful diagnostic and scientific information since the presence or absence of a specific nucleic acid can directly or indirectly correlate with one or more cells of observable structure and morphology, and, in this way, provide a basis for clinical diagnosis and prognosis.

The method for detecting a target nucleic acid fragment directly from a specimen is comprised of multiple steps which are to be performed in the specific order listed. A specimen, usually obtained from a patient, is first deposited onto a slide. The sample is fixed onto the slide with fixative. The fixative comprises one of two possible sets of components, either methanol-acetic acid at a ratio of about 99:1 to 80:20, or formalin-acetic acid at a ratio of about 99:1 to 80:20. Once the sample is fixed, the nucleic acids of the sample are contacted with a probe complex specific for the target nucleic acid fragment, under conditions appropriate for hybridization. The probe complex is comprised of a nucleic acid sequence which is sufficiently complementary to the target nucleic acid to hybridize with the target nucleic acid under stringent conditions. The probe complex is also derivatized with a moiety which serves as a marker for probe presence. After an adequate period of hybridization, the non-hybridized probe is rinsed from the sample. The sample is then rinsed with Evans Blue to counter stain the host cells, so as to see clearly fluorescent labeled probe(s) bound to specific nucleic acids of the pathogens which may be present within the sample (e.g. within the cells of the sample). Any probe which is hybridized to the nucleic acid of the fixed sample is then visually detected by microscopy. The presence of probe within the sample is an indication of the presence of the target nucleic acid fragment. Counterstaining the pathogen cells concurrently with the in situ hybridization assay enhances the method by allowing a clearer determination of the location of the target nucleic acid within the sample. Such information helps, for example, to provide a clearer determination of background hybridization. This sensitivity of this method has been determined to be detection of at least 10 copies of target nucleic acid.

This method is suitable for use with any specimen obtained from a patient. This includes, without limitation, whole blood, serum, plasma, sputum, urine, breast milk, cerebral spinal fluid, and tissue. This method is also suitable for detection of a pathogen within the cells of an insect vector. The sample is deposited onto the slide by standard means, and is then fixed onto the slide using either the methanol-acetic acid fixative or the formalin-acetic acid fixative.

The purpose of fixing cells or tissue is to preserve the morphology of the cells or tissue such that RNA is retained within the cellular matrix under the rigorous conditions experienced during in situ hybridization. The preferred method thus utilizes a fixative which is able to preserve and retain nucleic acids of the cell and at the same time cross-link and/or precipitate the proteins in the cellular matrix such that the cell or tissue remains substantially in open configuration for probe penetration and subsequent hybridization.

The novel fixatives described here are mixtures of the compounds methanol and acetic acid, or formalin and acetic acid (both mixtures at a ration of from about 99:1 to 80:20). When these fixatives are used, no pretreatment, such as with proteases, acetic anhydride, etc., is required. In a preferred embodiment, the fixative is methanol-acetic acid at a ratio of 95:5. In another embodiment, the fixative is formalin-acetic acid at a ratio of 95:5.

As used herein, the term probe refers to synthetic or biologically produced nucleic acids (DNA, RNA, or the equivalents thereof) which are engineered to contain specific nucleotide sequences which hybridize under stringent conditions to target nucleic acid sequences. The probe complex is defined as a probe which is derivatized with a marker moiety for detection. The marker moiety is attached at either the 5' end, the 3' end, internally, or in any possible combination thereof. The preferred moiety is an identifying label such as radiolabel (e.g. $P^{32}$, $I^{125}$, $H^3$), a biotin moiety, or a fluorescein moiety. Alternatively, the oligonucleotide has a poly-deoxynucleotide tail which is used for detection of the probe complex. The probe complex may also be comprised of a plurality of different nucleic acid sequences each labeled with a marker moiety. It may be beneficial to label the different nucleic acid sequences each with a different marker moiety.

The nucleotide sequence of the oligonucleotide is substantially similar to at least a portion of the target nucleic acid. The target nucleic acid is either a nucleic acid normally present within the fixed cell or tissue, or alternatively which is not normally present in the cell or tissue and is associated with an abnormal or pathological state. Each probe complex molecule is preferably comprised of a DNA or RNA fragment ranging in size from about 10–50 nucleotides.

The quantity of the total probe complex used is a predetermined amount which should exceed the estimated amount of the available target believed to be within the sample (about 100:1) in order to drive the hybridization reaction efficiently and to promote a high rate of probe:target annealing.

The probe complex is contacted with the nucleic acids of the fixed sample, generally by adding a solution of probe complex onto the sample. Conditions appropriate for hybridization are solutions which provide the appropriate buffered environment. Some examples of appropriate hybridization buffers are:

1) a buffer which is between about 10% and 50% formamide, 2×SSC (pH 7.4), and 1% NP40;
2) a buffer which is between about 1.5 M and 4 M GuSCN buffer;

5 M GuSCN stock buffer is made from 5 M GuSCN, 100 mM Tris-HCl (pH 7.8), 40 mM EDTA, 1% NP40. This stock buffer is diluted to the indicted molarity of GuSCN by the addition of deionized water to produce the above referenced GuSCN buffer molarities.

3) a buffer which is between about 2 to 6 M GuHCl buffer. 8 M GuHCl stock buffer is made from 8 M GuHCl, 200 mM Tris-HCl, (pH 7.8), 40 mM EDTA, 1% NP40. This stock buffer is diluted to the indicated molarity of GuHCl by he addition of deionized water to produce the above referenced GuHCl buffer molarities.

The specific concentration of hybridization buffer varies with the probe complex nucleic acid sequence and length. The exact concentration of buffer used is dependent on the Tm of the probe, probe sequence, probe length, and hybridization temperature, and can be determined by one of skill in the art through the course of no more than routine experimentation.

It should be appreciated that the use of formamide in the hybridization fluid allows hybridization to be carried out at a much lower temperature than standard hybridization protocols. Hybridization of an average probe complex specifically to the target (and not to host cells) in aqueous hybridization fluid such as sodium chloride would generally require a temperature of 60–65° C. The same hybridization performed at 42° C. in hybridization fluid 1) above, would provide specificity.

It should be appreciated that use of GuSCN also allows hybridization to be carried out at a much lower temperature than standard hybridization protocols. For instance, in an average procedure, hybridization of the probe specifically to the target (and not to host cells) in aqueous hybridization fluid such as sodium chloride would require temperatures of approximately 60–65° C. However, hybridization performed in The GuSCN or GuHCl hybridization buffer above, at 37° C. will provide specificity of hybridization.

After hybridization is complete, the non-hybridized probe is rinsed from the sample, generally by applying a series of washes with a wash buffer. It is within the means of those skilled in the art to determine appropriate wash buffers. One such wash buffer is 0.3 M sodium chlcride, 0.03 M sodium citrate, and 0.5% NP40. Another wash buffer is phosphate buffered saline (PBS).

After rinsing, the sample may be stained with Evans Blue. This counter-staining allows the visualization of organisms within the cells which contain the hybridized probes. This staining step is generally applied when a fluorescent labeled probe is used to detect nucleic acids which are specific for a pathogen. Although helpful, the Evans Blue counter-stain is not required for the above method.

The probe is detected by means suitable for the specific moiety used to label the probe complex. The preferred method for detecting a fluorescent-labeled probe, employs special filters such as a blue filter (fluorescent labeled probe) and a green filter (for rhodamine-X or Texas red labeled probe). It should be recognized that hybridization of radio-labeled probes to targets can be detected by autoradiography. Biotin labeled probes can be detected by enzymatic detection systems and such detection systems are commercially available.

The method described above allowed simultaneous detection of different pathogens in a single clinical sample by performing one reaction with a probe complex which is comprised of a plurality of different nucleic acid sequences, each labeled with a different marker moiety. For simultaneous detection the oligonucleotides which are specific for the different nucleic acids (of the different pathogens) commonly present in a clinical specimen can be designed such that the Tm values of all the probe complex sequences are very similar. Each specific oligonucleotide is then labeled with a different detectable moiety (e.g. different fluorescent moieties). Hybridization is performed with the multiple components of the probe complex. The hybridized sample is processed as described above and the sample is observed by means appropriate for detection of the different labeled oligonucleotides of the probe complex (e.g. viewed using appropriate filters if different fluorescent moieties are used) to detect which of the pathogen is present in the sample.

It will be recognized by practitioners ordinarily skilled in this art that the novel in situ hybridization protocol described herein is compatible with all previously known methods of detection as well as the one described herein. The in situ hybridization protocol has been streamlined so that fewer manipulations are necessary and can therefore be performed in a short time. It is expected that the reagents will be provided in a kit form to practice the protocol which has been optimized for simplicity and for compatibility with a wide variety of detection methods. It is also expected that such prepared kits containing specifically prepared reagents and probes, will be applicable in clinical/diagnostic laboratories, where the ability to detect the presence (or absence) of specific nucleic acids would serve to positively or negatively identify pathological states characterized by the presence of specific genes.

The current diagnosis of many cellular pathologies depends on microscopic evaluations, cellular morphological parameters, staining characteristics, and the presence (or absence) of certain antigens. Many of these methods of diagnosis are not entirely accurate or sufficiently sensitive. In situ hybridization using the above described protocol and pathogen specific probes will allow easier and more accurate identification of pathogens in samples.

The present invention provides a simple in situ hybridization protocol which provides enhanced sample processing, hybridization and detection characteristics as well as improved morphological preservation of sample as compared to previously described protocols. The improvements include:
1) Maximizing the sensitivity of the assay by increasing efficiency of hybridization and detection of specific "signal" and decreasing non-specific "noise".
2) Maximizing the retention of the target nucleic acid sequences in the cell or tissue sample.
3) Maximizing preservation of the other biochemical and morphological characteristics of the cell or tissue sample.
4) Minimizing both the total time and steps required for the protocol.

Some specific features and advantages of the method described which differentiate it from the prior art are as follows: It requires a simple fixation protocol. It eliminates a number of pre-hybridization steps of cells or tissue sample without any adverse effects. The following steps generally used in art, have been eliminated or improved upon: Incubation with proteases has been eliminated. Prehybridization has been eliminated. Incubation in acetic anhydride has been eliminated. This procedure allows for reduced hybridization times and a reduction in post hybridization rinses from several hours to a few minutes a room temperature. This procedure allows for the use of non-radiolabeled probes, which have a much longer shelf life and do not require special storage space. Either direct detection system using dark field microscopy can be used, or a few simple steps can be added for detection with light microscopy.

A preferred use of the above method is in the detection of *Babesia microti* in infected blood. It will be understood and appreciated by one of skill in the art that the novel methodology is equally applicable to a wide variety of other systems, cells, tissue cultures and tissues for hybridization of specific nucleic acids of interest with concomitant preservation of cell integrity and morphology.

An oligonucleotide probe comprised of DNA sequence which specifically hybridizes to the small sub-unit of the ribosomal RNA of *B. microti* is preferably used in the detection of the presence of *B. microti* in cells. A suitable probe complex is:

5'-Fluorescein-GCCACGCGAAAACGCGCCTCGA-Fluorescein-3' (SEQ ID NO: 1)

In one embodiment, this probe complex is contacted to the nucleic acids of the fixed sample in a hybridization buffer of 2.5 M GuSCN, 50 mM Tris (pH 7.8), 20 mM EDTA and 1% NP40 at 37° C. In an alternate embodiment, this probe complex is contacted to the nucleic acids of the fixed sample in a hybridization buffer of 50% formamide, 2×SSC (pH 7.4), 20 mM EDTA, 1% NP40 at 42° C.

Other suitable oligonucleotide sequences for use in alternate probe complexes for the detection of Babesia species are:
B5: 5'-GCCACGCGAAAACGCGCC-3' (SEQ ID NO: 2)
B6: 5'-AATAAACGCCACGCGAAAAC-3' (SEQ ID NO: 3)
B7: 5'-GCCACGCGAAAACGCGCCTCGAG-3' (SEQ ID NO: 4)
B8-1: 5'-AATAAACGCAGCCAAGAC-3' (SEQ ID NO: 5)
B8-2: 5'-AATAAACGCAGCCAAGACAG-3' (SEQ ID NO: 6)

The sequences B5, B6, B7, and the complements thereof are suitable for detection of *B. microti*. B8-1, B8-2, and the complements thereof, are suitable for detection of B. WA-1. These and other oligonucleotide sequences which can be used in the specific detection of a target nucleic acid fragment in a specimen are listed in the U.S. Patent Application filed concurrently with the present disclosure, entitled "Improved Methods for Detecting a Target Nucleic Acid Fragment", the contents of which are incorporated herein by reference.

The ribosomal RNA sequence is chosen for use in the detection of the Babesia pathogens because of the high abundance of rRNA in *B. microti* cells (1,000–10,000 copies). Preferably the oligonucleotide of the probe complex is a DNA with a sequence complimentary to *B. microti* rRNA. The oligonucleotide is preferably labeled at the 3' and 5' end with fluorescein. It will be recognized that a RNA oligonucleotide probe can be used as well.

As discussed above, the quantity of the total probe is a predetermined amount which should exceed the estimated amount of the available rRNA believed to be within the sample (about 100:1) in order to drive the hybridization reaction efficiently and to promote a high rate of probe:target annealing. In quantitative terms, this requires that a probe comprised of a 30 nucleotide long oligonucleotide be used in concentrations ranging from 1–2 $\mu$g/ml to produce reliable signal above background.

It should be appreciated that use of GuSCN also allows hybridization to be carried out at a much lower temperature than standard hybridization protocols. Hybridization of the specified probe specifically to the target (and not to host cells) in aqueous hybridization fluid such as sodium chloride would require a temperature of 60–65° C. However, hybridization performed in The GuSCN or GuHCl hybridization buffer above, at 37° C. ensures specificity.

One of the advantages of the in situ hybridization method is that relatively small numbers of cells comprise a sample and large numbers of identical samples may be processed over a short period of time. The unique in situ hybridization method described is extremely simple. The methods of the present invention can also be applied to any kind of sample, including, without limitation, paraffin-embedded tissue sections, acetone fixed samples.

EXEMPLIFICATION

Example 1

Detection of *Babesia microti* in Infected Blood. Comparison of FISH vs. IFA and PCR Fluorescence in situ hybridization (FISH) analysis of the present invention was compared to the two step isolation and PCR detection method and indirect immunofluorescence analysis (IFA) in the detection of the pathogen *B. microti*. The FISH assay was designed to detect *B. microti* specific ribosomal RNA on a whole blood smear. The isolation and PCR assay was used to detect *B. microti* specific DNA from whole blood, using *B. microti* specific primers. (IFAs) for detection of *B. microti* IgG and IgM antibodies were performed on serum, from all the patients according to the manufacturer's recommendations.

Tests were performed on a total of 221 whole blood samples from patients suspected of Babesiosis. A FISH assay result was considered positive if either the trophozoite (ring) form of *B. microti* or the merozoite (spore) form of *B. microti*, or both forms were detected in the red blood cell. Samples were considered positive by IFA if the *B. microti* antibody titers were greater than 1:80.

The results of each test are presented in Table 1. Of the 221 samples tested by IFA, 38 samples were considered positive by IFA (titers of 1:80 or greater) and 183 samples were considered negative. As shown in Table 1, of the 38 samples determined positive by IFA, 13 were also determined positive by FISH. Of these 13 samples, 11 were also determined to be positive by PCR analysis. In addition, there were six samples which tested negative by FISH but tested positive by PCR analysis. The assay sensitivity of FISH was 34% as compared to IFA. PCR analysis sensitivity was 45%. Of the 183 samples which tested negative by IFA, 60 samples were determined to be positive by FISH. Of these 60, 45 were also determined to be positive by PCR analysis. In addition, 26 samples which tested negative by FISH tested positive by PCR analysis.

TABLE 1

Comparison of PCR, FISH and IFA for *Babesia microti*

| Samples | Samples | PCR (+) | FISH (+) | PCR + FISH |
|---|---|---|---|---|
| IFA (+) | 38 | 17 | 13 | 11 |
| IFA (−) | 183 | 71 | 60 | 45 |
| # Samples | 221 | 87 | 63 | 56 |
| Percent (+) | 17.19% | 39.37% | 28.51% | 25.34% |

The discrepancy between the IFA results and FISH results is not surprising. Diagnosis based on antibody response requires the sero-conversion of the infected individuals towards production of anti-*B. microti* antibodies. At the height of Babesiosis, within weeks of the initial bite, a patient with fever may fail to exhibit antibody. The *B. microti* FISH assay detects parasite rRNA and at the same time is independent of the host immune response. Therefore, it can detect active infection. This may explains why 45 *B. microti* FISH and PCR positive samples were negative by IFA. In addition, there were 15 samples positive by FISH but negative by PCR. It is possible that these samples were PCR negative due to presence of inhibitors or due to DNA degradation during processing. It is also possible that the FISH method of detection is producing false positive results. Since these samples were IFA negative as well, we consider that these 15 samples may be false positives. Assuming that these 15 samples were "true negatives", the FISH assay still has a specificity of 93%.

Polyclonal antibody based test are not highly specific. In a previous study of 45 patients positive by IFA, 17 had no detectable *B. microti* specific DNA by PCR (Krause et al., *J. Clin Microbiol*. 34: 2014–2016 (1996)). In addition, antibodies often persist long after the parasite has cleared. FISH assay is a non-amplified, highly specific assay that detects *B. microti* specific rRNA directly on whole blood smears. Therefore, it is not surprising that 26/38 were positive by IFA but negative by FISH.

The discrepancy between the FISH results and the PCR results also is not surprising. FISH assay is a non-amplified assay that detects *B. microti* rRNA within red blood cells. *B. microti* PCR is an amplified assay that detects minute quantities of parasite DNA and at the same time is independent of the host immune response. In addition, PCR is not dependent on the viability of the organism. Therefore, PCR is more sensitive than FISH. This would explain why there were 32 samples positive by PCR but negative by FISH. This included six samples positive by IFA and 26 samples negative by IFA.

Based on the data presented above, 89 samples (40%) were considered true positives assuming PCR assay specificity as 100% and FISH assay specificity as 93%. The FISH assay monitors active infection, and has sensitivity of 67% as compared to PCR. In addition, the data clearly demonstrates that FISH is a more sensitive and specific than the IFA. These results indicate that the FISH technique of the present invention is very simple and reliable.

A variety of specimens with different pathogens—whole blood smears, infected tick mid guts pure cultures and tissue cultures have been tested via FISH assay to determine the general applicability of this methodology. In all specimens tested the FISH analysis provided clear, accurate results which were confirmed by other assays.

Methods

Fixation/Pretreatment of Cell.

Thin and thick blood smears were made from EDTA treated fresh blood by standard technique onto glass slides. The smears were air dried and stored at room temperature until the day of the experiment. The air dried smears were treated by a mixture of methanol:acetic acid (95:5) for 10 minutes at room temperature. Excess solution was removed, and the slides were air dried.

Hybridization Buffers and Hybridization.

Hybridization was performed in either (1) 50% formamide, 2×SSC, pH 7.4, 1% NP40, and 1–2 µg/ml of the *B. microti* probe, or (2) 2.5 M GuSCN, 50 mM Tris, 20 mM EDTA, 1% NP40, pH 7.8, and 1–2 µg/ml of the *B. microti* probe.

25 µl of the hybridization fluid (1) was applied per slide. The slide was then covered with a cover-slip and incubated in a humid chamber at 42° C. for 30 minutes. (Note: if 25 μl of hybridization fluid (2) was applied per slide, the hybridization was done at 37° C. for 30 minutes.

Probe Sequence.

An oligonucleotide DNA probe complimentary to *B. microti*, labeled at 3' and 5' with fluorescein was synthesized by the standard method. The nucleic acid sequence of the probe is listed below:

5' —Fluorescein-GCCACGCGAAAACGCGCCT CGA—Fluorescein-3' (SEQ ID NO: 1)

Post Hybridization Rinses.

After completion of the hybridization, cover slips were removed and slides were washed three times individually with a wash buffer, pH 7.4, (0.3 M sodium chloride, 0.03 M sodium citrate, 0.5% NP40) at room temperature, for 2 minutes each. After the third wash, slides were rinsed in phosphate buffered saline, pH 7.2 (PBS) for 2 minutes at room temperature. Finally the washed sides were placed in a Coplin jar containing PBS and Evans Blue (30 ml PBS+3 drops of 0.1% Evans Blue in PBS). The slides are blotted dry and 2 drops of fixative was added per slide and covered with a cover slip. The slides were stored for about 10 minutes in darkness at room temperature and then viewed under dark field at 40x.

Method for Detecting in situ Hybridized Cells.

The fluorescent-labeled probe was detected by microscopy using special filters such as a blue filter (fluorescent labeled probe) and a green filter (for rhodamine-X or Texas red labeled probe).

Detection of *B. microti* DNA from Clinical Samples by PCR.

EDTA treated whole blood samples were treated with 5 M GuSCN buffer, pH 7.4, (100 mM Tris-HCl, pH 7.8, 40 mM EDTA, 5 M GuSCN and 1% Sarkosyl). The GuSCN concentration was adjusted to 2.5 M, with either water or TE (pH 7.8). The sample tubes were vortexed for 30 seconds and then heated at 85° C. for 10 minutes to denature DNA.

The temperature was reduced to 65° C. and the samples were allowed to equilibrate for 5 minutes. 40 μl of *B. microti* DNA probe B2 (1 μg/ml), labeled with biotin at the 5' end, was added to each sample. Sample plus probe was left at 65° C. for another 5 minutes. The sample was then incubated at 37° C. for more than three hours to allow hybridization of the probes to the complementary *B. microti* specific nucleic acids. The probe and any hybridized nucleic acids was then captured onto paramagnetic particles derivatized with streptavidin (10 μg/ml to 100 μg/ml) by diluting the GuSCN concentration to 1.25 M GuSCN. The probe bound particles were washed once with GuSCN wash buffer (1.25 M GuSCN buffer, 0.1% BSA), followed by 2 washes with 0.1xSSCN buffer (0.015 M NaCl, 0.0015 M Na Citrate, 0.1% BSA, 0.1% NP40, pH 7.4), and then once with 0.1xSSC buffer (0.015 M NaCl, 0.0015 M Na Citrate, pH 7.4). Following the wash steps, the nucleic acids hybridized to the probe was released by the addition of 100 μl deionized water.

10 μl of the solution containing the released nucleic acids was subjected to PCR amplification using standard procedures. The detection limit was observed to be one organism per sample tested.

Probes and PCR Primers for PCR Detection of *B. microti*.

The selection probe used was a DNA oligonucleotide labeled at the 5' end with biotin, the nucleotide sequence 5'-ATAGGTCAGAAACTTGAATGATACATCGCCGGC-3' (SEQ ID NO: 7).

The PCR primers were DNA oligonucleotides with the sequence 5'-GTTATAGTTTATTTGATGTTCGTT-3' (SEQ ID NO: 8) and 5'-AATAAACGCCACGCGAAAAC-3' (SEQ ID NO: 3).

Immunofluorescence Assay.

Immunofluorescence assays for the detection of *B. microti* IgG and IgM antibodies were performed on serum from all patients, according to the manufacturer's recommendations (MRL Diagnostics, CA).

What is claimed is:

1. A method for detecting a target nucleic acid fragment in a specimen obtained from a patient by in situ hybridization comprising the steps:
   a) depositing a sample of the specimen onto a slide;
   b) fixing the sample onto the slide with fixative, the fixative comprising either methanol-acetic acid at a ratio of from 99:1 to 80:20, or formalin-acetic acid at a ratio of from 99:1 to 80:20;
   c) contacting nucleic acids of the fixed sample with a probe complex that specifically hybridizes to the target nucleic acid fragment, under hybridization conditions;
   d) rinsing non-hybridized probe complex from the sample;
   e) staining the rinsed sample with Evans Blue; and
   f) visually detecting hybridized probe complex by microscopy, with the presence of the hybridized probe complex being an indication of the presence of the target nucleic acid fragment.

2. The method of claim 1 wherein the fixative is methanol-acetic acid 95:5.

3. The method of claim 1 wherein the fixative is formalin-acetic acid 95:5.

4. The method of claim 1 wherein the contacting of the probe complex and the nucleic acids of the fixed sample occurs in a buffer consisting essentially of from 10% to 50% formamide, 2×SSC (pH 7.4), and 1% NP40.

5. The method of claim 1 wherein the contacting of the probe complex and the nucleic acids of the fixed sample occurs in a buffer consisting essentially of 1.5 M to 4 M GuSCN buffer.

6. The method of claim 1 wherein the contacting of the probe complex and the nucleic acids of the fixed sample occurs in a buffer consisting essentially of 2 M to 6 M GuHCL buffer.

7. The method of claim 1 wherein the probe complex comprises an oligonucleotide linked to a fluorescent marker.

8. The method of claim 1 wherein the probe complex comprises an oligonucleotide linked to biotin.

9. The method of claim 1 wherein the probe complex comprises an oligonucleotide which has a poly-deoxynucleotide tail.

10. The method of claim 1 wherein the target nucleic acid fragment is a nucleic acid from a pathogen with which the patient is suspected of being infected.

11. The method of claim 10 wherein the pathogen is *B. microti* and the probe complex is 5'-Fluorescein-GCCACGCGAAAACGCGCCTCGA (SEO ID NO: 1)-Fluorescein-3'.

12. The method of claim 11 wherein the contacting of the probe complex and the nucleic acids of the fixed sample occurs in a buffer consisting essentially of 2.5 M GuSCN, 50 mM Tris (pH 7.8), 20 mM EDTA and 1% NP40 at 37° C.

13. The method of claim 11 wherein the contacting of the probe complex and the nucleic acids of the fixed sample occurs in a buffer consisting essentially of 50% formamide, 2×SSC (pH7.4), 20 mM EDTA, and 1% NP40 at 42° C.

14. The method of claim 7 wherein the probe complex comprises a plurality of different nucleic acid sequences, each labeled with a different fluorescent marker.

15. The method of claim 10 wherein the pathogen is Babesia and the probe complex comprises one or more of the following oligonucleotides or their complements:

B5: 5'-GCCACGCGAAAACGCGCC-3' (SEQ ID NO: 2)

B6: 5'-AATAAACGCCACGCGAAAAC-3' (SEQ ID NO: 3)

B7: 5'-GCCACGCGAAAACGCGCCTCGAG-3' (SEQ ID NO: 4)

B8-1: 5'-AATAAACGCAGCCAAGAC-3' (SEQ ID NO: 5), or

B8-2: 5'-AATAAACGCAGCCAAGACAG-3' (SEQ ID NO: 6).

16. The method of claim 15 wherein the pathogen is *B. microti* and the probe complex comprises one or more of the following oligonucleotides or their complements:

B5: 5'-GCCACGCGAAAACGCGCC-3' (SEQ ID NO: 2)

B6: 5'-AATAAACGCCACGCGAAAAC-3' (SEQ ID NO: 3), or

B7: 5'-GCCACGCGAAAACGCGCCTCGAG-3' (SEQ ID NO: 4).

17. The method of claim 15 wherein the pathogen is B. WA-1 and the probe complex comprises 5'-AATAAACGCAGCCAAGAC-3' (SEQ ID NO: 5).

18. The method of claim 1 wherein the specimen is whole blood.

19. The method of claim 1 wherein the specimen is serum.

20. The method of claim 1 wherein the specimen is plasma.

21. The method of claim 1 wherein the specimen is sputum.

22. The method of claim 1 wherein the specimen is urine.

23. The method of claim 1 wherein the specimen is cerebral spinal fluid.

24. The method of claim 1 wherein the specimen is tissue.

25. The method of claim 1 wherein the specimen is breast milk.

26. The method of claim 1 wherein the specimen is obtained from a tick.

* * * * *

UNITED STATES PATENT AND TRADEMARK OFFICE
CERTIFICATE OF CORRECTION

PATENT NO. : 6,165,723
DATED : December 26, 2000
INVENTOR(S) : Jyotsna S. Shah & Nick S. Harris It is certified that error appears in the above-indentified patent and that said Letters Patent is hereby corrected as shown below:

Claim 11, line 6, delete "(SEO ID NO:" and substitute therefor ---(SEQ ID NO:---.

Signed and Sealed this

First Day of May, 2001

Attest:

NICHOLAS P. GODICI

*Attesting Officer*    Acting Director of the United States Patent and Trademark Office